United States Patent [19]

DiBella

[11] Patent Number: 5,006,585
[45] Date of Patent: Apr. 9, 1991

[54] STAIN-RESISTANT PLASTICIZER COMPOSITIONS AND METHOD OF MAKING SAME

[75] Inventor: Eugene P. DiBella, Piscataway, N.J.

[73] Assignee: Huls America Inc., Piscataway, N.J.

[21] Appl. No.: 402,570

[22] Filed: Sep. 5, 1989

[51] Int. Cl.$^5$ .................... C08K 5/09; C07C 69/76
[52] U.S. Cl. .................... 524/293; 524/569; 560/112; 568/852
[58] Field of Search .................... 568/852; 560/112; 524/293, 287

[56] References Cited

U.S. PATENT DOCUMENTS

| | | | |
|---|---|---|---|
| 2,454,274 | 11/1948 | Daly et al. | 260/476 |
| 2,625,563 | 1/1953 | Bell . | |
| 2,700,656 | 1/1955 | Emerson et al. | 260/31.6 |
| 2,766,266 | 10/1956 | Emerson et al. | 260/410.6 |
| 3,072,591 | 1/1963 | Fath | 260/31.6 |
| 3,158,585 | 11/1964 | Kelso et al. | 260/30.4 |
| 3,160,599 | 12/1964 | Scullin | 560/112 |
| 3,211,561 | 10/1965 | Gearhart et al. | 106/180 |
| 3,361,700 | 1/1968 | Archer et al. | 560/112 |
| 3,414,609 | 12/1968 | Hagemeyer et al. | 260/475 |
| 3,433,661 | 3/1969 | Maggart et al. | 106/316 |
| 3,562,300 | 2/1971 | Chao et al. | 260/398 |
| 3,652,610 | 3/1972 | Coopersmith et al. | 260/410.6 |
| 3,671,654 | 6/1972 | Nosler et al. . | |
| 4,024,164 | 5/1977 | Bailey et al. | 260/347.5 |
| 4,074,058 | 2/1978 | Bailey et al. | 560/105 |
| 4,107,192 | 8/1978 | Bailey et al. | 260/410.5 |
| 4,405,646 | 9/1983 | Boden et al. | 426/3 |
| 4,656,214 | 4/1987 | Wickson | 524/287 |

FOREIGN PATENT DOCUMENTS 1011865 7/1957 Fed. Rep. of Germany .
767455 2/1957 United Kingdom .

OTHER PUBLICATIONS

Kirk Othmer, Encyclopedia Chem. Tech., 2nd Ed, p. 678-9 (1966).
CA:101:87140w, Aberhart et al., 1984.
CA, vol. 99, 53768g, abstract of Japanese 58-49377.
CA, vol 82, 139395u, abstract of Japanese 74-94620.
CA, vol. 88, 74921q, abstract of Japanese 77,101,253 (52-101253).
CA, vol. 91, 140357a, abstract of Japanese 79-46708.
CA, vol. 54, 2172g, abstract of Ger. Pat. 1,011,865.
CA, vol. 75, 117725e, Mazet et al.
CA, vol. 78, 15503a, abstract of U.K. Patent 1,290,094.
Morison et al., "Effect of Molecular Configuration on Esterification Rates of Certain Alcohols and Glycols . . . ," ACS, Div. Org. Coatings & Plastics, Preprints 21, No. 1, 159-70 (1961).
Mazet et al., "Methyl Group Migration in Acid-Catalyzed Dehydration of . . . Diols," Bull. Soc. Chim Fr., 1971 (7), 2656-62.
Bailey et al., "Preparation of Some Mixed Diesters of Aliphatic Diols and Their Evaluation as Plasticizers," JAOCS, 53:176-78 (1976).
Wickson et al., "Structural Studies on Low Volatility PVC Plasticizers Based on Trialkylacetic Acids (Neo-Acids)," SPE ANTEC Preprint, pp. 238-42 (1969).

Primary Examiner—Joseph L. Schofer
Assistant Examiner—Mark D. Sweet
Attorney, Agent, or Firm—James P. Scullin

[57] ABSTRACT

Mono- and di-esters of 2,2,4-trimethyl-1,3-pentanediol and benzoic acids are useful plasticizers for vinyl chloride polymers, and other polymers, particularly for imparting improved stain resistance to plasticized compositions. Novel processes for preparing the esters are disclosed.

7 Claims, No Drawings

STAIN-RESISTANT PLASTICIZER COMPOSITIONS AND METHOD OF MAKING SAME

BACKGROUND OF THE INVENTION

1. Field of the Invention

This invention pertains to esters of 2,2,4-trimethyl-1,3-pentanediol and benzoic acid or alkyl-substituted benzoic acids; to processes for making said esters; and to the use of said esters as stain-resistant plasticizers for poly (vinyl chloride) and other polymers, especially for poly (vinyl chloride)-based floor-covering compositions.

2. Description of the Prior Art

Many polymeric resins, such as vinyl chloride polymers by way of example, are hard and even brittle in their natural state, in the absence of plasticizers. Although such unplasticized resins can often be used to manufacture useful articles of commerce, such as pipes, house siding, phonograph records, and so forth, for many other applications plasticizers are required in order to lower processing temperatures or to impart flexibility and softness to end products made from such resins. In addition to improving processability and imparting flexibility, suitable plasticizers must be compatible with the resin, must be thermally stable during processing and under end-use conditions, should not impart substantial color or odor, and should be permanent, i.e., should be resistant to removal from the resin due to volatilization, extraction by solvents, or migration into any material in contact with the plasticized resin.

Polymers and copolymers of vinyl chloride are widely used as plasticized compositions, and a very large number of compounds have been found to be useful, in varying degrees, as plasticizers for such resins. In particular, the most useful of such plasticizers include diesters of alkanols and dicarboxylic acids, polyesters derived from diols and dicarboxylic acids, and, to a lesser extent, diesters of diols and monocarboxylic acids.

One of the major applications for plasticized vinyl chloride compositions is as floor coverings and wall coverings, for purposes of both protection and decoration. In these applications in particular, a further required attribute of a suitable plasticizer is to impart resistance to staining when contacted by such things as road tar, crayons, shoe polish, foodstuffs, and so on.

Floor and wall covering compositions based on vinyl chloride polymers are manufactured by various methods, especially by calendering or by spread—coating of a liquid dispersion—a plastisol or an organosol—onto a substrate. In the latter case, a still further requirement must be met in order for a plasticizer to be suitable: the plasticizer must have a sufficiently low viscosity to impart fluidity to the plastisol or organosol, must have solvating power for the resin at elevated temperatures sufficient to readily fuse resin and plasticizer into a coherent mass but, at the same time, its solvating power for the resin at ordinary room temperature should be low enough to avoid undue increase in the viscosity of the dispersion after preparation and during storage. A large and rapid viscosity increase may make it difficult, or impossible, to spread the dispersion properly onto the substrate. As an example, butyl benzyl phthalate has many of the desirable attributes of a plasticizer for vinyl chloride polymers, including fairly good stain resistance, but its solvating power at ordinary temperatures causes rapid viscosity increase in plastisols and therefore limits its applicability in such dispersions.

There are numerous disclosures in the prior art of plasticizers for vinyl chloride polymers (PVC) and other resins that are said to impart stain resistance, some of which are esters of benzoic acid and some of which are diesters of 2,2,4-trimethyl-1,3-pentanediol (hereinafter referred to as TMPD). In U.S. Pat. No. 3,158,585 Kelso et al discloses phthalic acid esters of various alcohols as stain resistant plasticizers. In U.S. Pat. No. 3,160,599 Scullin discloses the stain resistance of the monoisobutyrate monobenzoate ester of TMPD. Bailey et al, *J. Amer. Oil Chem. Soc.* vol. 53, 176–178 (1976) reports on the utility as PVC plasticizers of mixed esters of ethylene glycol, diethylene glycol, and 2-butene-1,4-diol wherein one of the ester moieties was benzoate. U.S. Pat. Nos. 4,024,164; 4,074,058; and 4,107,192 to Bailey contain related disclosures.

Wickson et al, *Soc. Plastic Eng. Preprint, Annual Technical Conference*, p. 238-42 (1969) compares the properties as PVC plasticizers of ethylene glycol diesters. In U.S. Pat. No. 2,454,274 Daly et al discloses the utility of ethylene glycol acetate benzoate as a plasticizer for esters and ethers of cellulose.

In U.S. Pat. Nos. 2,700,656 and 2,766,266 Emerson et al discloses diesters of substituted 1,5-pentanediols, in which one ester group is an aromatic acid moiety and the other an aliphatic acid moiety. In U.S. Pat. No. 3,072,591 there are disclosed, as PVC plasticizers, aromatic-aliphatic carboxylic acid esters of a polymethylolalkane.

U.S. Pat. No. 3,433,661 to Maggart et al discloses complex monoesters derived from aromatic hydrocarbons, formaldehyde, and monocarboxylic acids as stain resistant plasticizers. U.S. Pat. No. 3,562,300 to Chao et al discloses the use of neoalkylpolyol esters of neoacids and straight or branched chain aliphatic acids as plasticizers.

U.S. Pat. No. 3,652,610 Coopersmith discloses plasticizers derived from the reaction of a hindered acid glycol monoester and di- or tri-basic acids. Japanese Patent Publication 52-101253 discloses as plasticizers polyalkylene glycol esters containing 1-14 ether bonds, and having one benzoic acid ester group and one aliphatic acid ester group. In U.S. Pat. No. 4,656,214 Wickson discloses stain resistant plasticizers that are diesters of ethylene glycol, propylene glycol, or 1,4-butanediol in which one ester group is a benzoate or toluate moiety, and the other a neoacid moiety. This reference also contains an incidental disclosure of plasticizer that is a mixture of diesters of TMPD, including TMPD dibenzoate as one of the lesser components.

In processes involving TMPD as a reactant, the thermal instability of this glycol under various conditions must be taken into account. Thus, the review of TMPD in the Encyl. Chem. Tech. (Kirk-Othmer), 2nd Ed. p. 679 (1966) points out that TMPD diesters undergo pyrolysis to the corresponding monoesters of 2,2,4-trimethyl-3-penten-1-ol. P. Morison and J. E. Hutchins, Am. Chem. Soc., Div. Org. Coatings Plastics Chem.; Preprints 21, No. 1, 159-70 (1961); CA. 57, 15272 e, reported that, among various glycols studied, TMPD was the most prone to thermal degradation.

B. Yoemans, Brit. 1,290,094 (1972); CA. 78, 15503a produced 2,2,4-trimethylpenten-1-isobutyrate by acid catalysed dehydration of a mixture of TMPD isobutyrates, TMPD diisobutyrate and TMPD itself. In related work, M. Mazet and M. Desmaison-Brut, Bull. Soc. Chim. Fr. 1971 (7) 2656; CA. 75, 117725e reported that the acid-catalysed dehydration of the secondary hydroxyl group of TMPD is also accompanied by some methyl migration from $C_2$ to $C_3$.

Instability under basic conditions also was described by E. Harrer and K. Ruhl, Ger. 1,011,865 (1957). Thus heating TMPD with potassium hydroxide at 145° C. reversed the process of its formation by producing isobutyraldehyde, isobutyl alcohol and isobutyrate ion.

Despite the inherent instability associated with the structure of TMPD, fair-to-excellent results have been achieved in preparing aliphatic diesters, with acidic conditions appearing the most favorable. Thus, TMPD diacetate was prepared in 93% yield by H. Nosler and H. Schnegelberger, U.S. Pat. No. 3,671,654 (1967); CA. 78, 75876j, by the action of acetic anhydride at 120–130° C. in the presence of p-toluenesulfonic acid. TMPD diformate has also been prepared using sulfuric acid as a catalyst for the reaction of TMPD with excess formic acid by R. Boden and M. Licciardello, U.S. Pat. No. 4,405,646 (1983); CA. 100, 5039n, but no yield was reported.

A. Bell, U.S. Pat. No. 2,625,563 (1953); CA. 47, 11229b, prepared the bis 2-ethylbutanoic and 2-ethylhexanoic esters at 60% and 42% yields respectively via uncatalysed esterifications of TMPD with the corresponding acids at 200°–210° C. The bis decanoic and tridecanoic esters were also prepared by A. Bell and G. Lappin, Brit. 767,455; CA. 51, 13379i, but no experimental details were provided.

TMPD diesters have also been prepared by transesterification. Thus in Japan Kokai Tokkyo Koho JP 58 49377 (83 49 377) (1983); CA. 99, 53768g, the p-toluenesulfonic acid-catalysed reaction of TMPD with ethylene carbonate at 110° C. led to a 93% yield of the cyclic carbonate ester, i.e. a disubstituted TMPD ester derivative.

T. Ogawa et al, Japan Kokai Tokkyo Koho 79 46708 (1979); CA. 91, 140357a, prepared TMPD diisobutyrate in 96% yield via the transesterification reaction of TMPD with isobutyl isobutyrate using tin or titanium, Lewis acid-type catalysts at 120°–250° C. With a basic system employing sodium hydroxide catalysis, the yield was only 64%. A similar basic system for preparing TMPD diisobutyrate from TMPD and isobutyl isobutyrate, in the presence of sodium hydroxide in isobutyl alcohol at 120°–170° C., was employed by T. Kojima et al., Japan Kokai 74 94620 (1974); CA. 82, 139395u. No yield was reported, however.

SUMMARY OF THE INVENTION

According to the present invention, monoesters and diesters of 2,2,4-trimethyl-1,3 pentanediol (TMPD) and benzoic acid and/or alkyl-substituted benzoic acids have been found to be useful and effective plasticizers for thermoplastic resins and for synthetic rubbers. They are particularly useful as plasticizers for vinyl resins, i.e., homopolymers and copolymers of vinyl chloride. When employed as plasticizers for vinyl resins, these esters impart a high degree of stain resistance, and provide plastisols and organosols having good resistance to viscosity increase during storage at ordinary temperatures. These features make the plasticizers of particular utility in the manufacture of floor coverings, wall coverings, and countertop surfaces. In addition, the esters of this invention are useful as general purpose plasticizers, in applications wherein stain-resistance is not of prime concern. The esters are also useful as synthetic lubricants, such as lubricants for machinery, metal working or textile fibers, and as functional fluids such as automatic transmission fluids.

The fact that the monoesters of TMPD are compatible with vinyl resins and are efficient and stain-resistant plasticizers for such resins is unexpected and surprising. It is conventional wisdom in this art that ester plasticizers, in order to be and remain compatible, should be essentially completely esterified and free from unreacted hydroxyl or carboxylic acid groups. By way of contrast to this, TMPD monobenzoate has a hydroxyl content of about 6.8% (a hydroxyl number of about 224).

Two processes are provided for the preparation of the novel monoesters: via benzoylation in an amine such as pyridine, and via base-catalyzed transesterification of TMPD, or a lower alkyl ester of TMPD, and an ester of benzoic acid or alkyl-substituted benzoic acid.

The diesters of the invention are also prepared by the novel process of transesterification in the presence of a base as catalyst. In contrast to prior art processes, wherein acidic conditions have been preferred and wherein thermal instability of TMPD and of its diesters have been found to be a problem, base-catalyzed transesterification provides a means of obtaining TMPD benzoates and alkyl-substituted benzoates in high yields and at excellent selectivities. Products of high diester content can be produced, if desired. The transesterification can be carried to above 90% diester, preferably by using a combination catalyst system, as will be described. Comparative examples using acid-catalyzed processes are provided, that gave lower yields of, and selectivities for, TMPD benzoate products together with accompanying by-products that resulted from degradation of the TMPD moiety.

DETAILED DESCRIPTION OF THE INVENTION

Diesters of TMPD and benzoic acid and/or alkyl-substituted benzoic acids are obtained in high yield by a process of transesterification of TMPD, or of an ester of TMPD and one or more monocarboxylic acids having from 1 to about 4 carbon atoms, with an ester having the formula

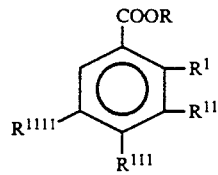

wherein $R$ = a $C_1$-$C_4$ alkyl, alkenyl or alkynyl group, and $R^1$, $R^{11}$, $R^{111}$ and $R^{1111}$ are any combination of H and alkyl groups having 1–4 carbon atoms, in the presence of a catalytic amount of a base.

By employing the novel process disclosed herein it is possible to prepare the diesters at yields of at least about 45 mole %, and up to greater than 90 mole %, based on TMPD charged, which corresponds to yields of total ester (combined di- and mono-esters) of from about 84 mole % up to greater than 98 mole % based on TMPD charged, depending on the base or combination of bases employed as the catalyst. The resultant products have a total ester content of greater than 98 weight %, and a diester content ranging from about 60 weight % to about 97 weight %. The principal ingredient of the products, other than diester, consists of monoesters of TMPD. Although the mixtures of diesters and monoesters, having a diester content of about 60 weight % or higher, are suitable for use (as plasticizers, for example) without further separation, it will be obvious to those skilled in the art that, if desired, the monoesters can be removed by known techniques (e.g. by fractional distillation) to obtain products of even higher diester content, up to essentially 100% by weight.

The reaction can be run at temperatures from about 30° C. to about 150° C. as desired, although a range of from about 90° C. to about 105° C. is preferred. It will be understood that molar ratios of TMPD (or a lower ester of TMPD) to benzoic acid ester of about ½ will be employed in order to obtain the desired diester product, although this is not critical and can be modified to a reasonable degree without departing from the scope of the invention. A slight excess of the benzoic acid ester is preferred.

Although the free diol, TMPD, is the preferred reactant, derivatives of TMPD which would be converted to a TMPD anion under the conditions of base-catalyzed transesterification can also be used in the process of this invention. Such derivatives include TMPD esters where the acid moiety is, in turn, derived from a carboxylic acid which, as an ester formed during transesterification with the benzoic acid ester, would be sufficiently volatile to be removed from the reaction mass.

Examples of suitable benzoate esters that can be used as reactants include esters of methanol, ethanol, n-propanol, isopropanol, n-butanol, sec-butanol, tert-butanol, allyl alcohol, propargyl alcohol, crotyl alcohol, allylcarbinol, 3-butyn-1-ol, 2-butyn-1-ol, 3-butyn-2-ol, and methallyl alcohol, and benzoic acid and the following alkyl-substituted benzoic acids: 2-methylbenzoic acid, 3-methylbenzoic acid, 4-methylbenzoic acid, 2,3-dimethylbenzoic acid, 2,4-dimethylbenzoic acid, 2,5-dimethylbenzoic acid, 3,4-dimethylbenzoic acid, 3,5-dimethylbenzoic acid, 2,3,4-trimethylbenzoic acid, 2,3,5-trimethylbenzoic acid, 2,4,5-trimethylbenzoic acid, 3,4,5-trimethylbenzoic acid, 2,3,4,5-tetramethylbenzoic acid, 2-ethylbenzoic acid, 3-ethylbenzoic acid, 4-ethylbenzoic acid, 2,3-diethylbenzoic acid, 2,4-diethylbenzoic acid, 2,5-diethylbenzoic acid, 2,3,4-triethylbenzoic acid, 2,3,5-triethylbenzoic acid, 2-n-propylbenzoic acid, 4-sec-propylbenzoic acid, 4-n-butylbenzoic acid, 4-soc-butylbenzoic acid, 2-tert-butylbenzoic acid, 3-tert-butylbenzoic acid, 4-tert-butylbenzoic acid. Preferred reactants are the esters of 2-methyl, 3-methyl, or 4-methyl benzoic acid and any of the alcohols mentioned above. Particularly preferred is methyl benzoate. The use of a single benzoate ester is preferred, but combinations of any of the foregoing benzoate esters, in any proportions, are included in the scope of this invention.

Examples of suitable basic catalysts include the hydroxides, alkoxides, glycolates, amides, hydrides, and other comparably strongly basic anionic species of the alkali metals, or of the alkaline earth metals (excluding magnesium); and quaternary ammonium hydroxides and alkoxides.

The reaction can be carried out under any set of conditions at or below atmospheric pressure under which the volatile by-product of reaction, e.g. methanol, can be removed in order to shift the equilibrium and allow continuation of the transesterification reaction. This is preferably accomplished at subatmospheric pressure in the 10-100 mm Hg range. However, higher pressures can be employed in conjunction with nitrogen sparging to accomplish the same result. Monobenzoate esters of TMPD, including mono-esters of alkyl-substituted benzoic acids, having the formula

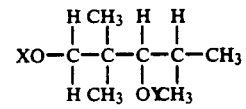

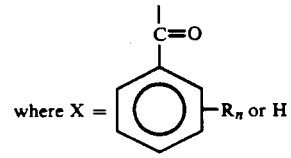

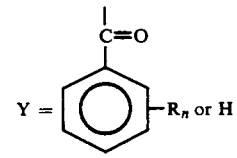

R is an alkyl group having from 1 to 4 carbon atoms, and n=0-5 and wherein either X or Y is H have been found to be excellent stain-resistant plasticizers, especially for homopolymers and copolymers of vinyl chloride. Either of the two isomers, or mixtures thereof in any proportions, can be used, as well as mixtures with any of the dibenzoates (or substituted dibenzoates) of TMPD previously described. The preferred monoesters are those wherein R=methyl and n=1, and wherein R=H. The latter, i.e. monoesters of benzoic acid itself, are particularly preferred. These monoesters can be prepared by means of transesterification, essentially in the manner as described above for the preparation of diesters, using 2,2,4-trimethyl-1,3-pentanediol as the diol, any of the above esters of benzoic acid or substituted benzoic acids, and a basic catalyst as previously described. It will be obvious that, in order to obtain monoesters in high yield, the mole ratio of TMPD to benzoate ester will be approximately 1/1, although the precise ratio is not critical. A slight excess of either reactant can be used, if desired.

A preferred method of preparing the novel monoesters is by means of benzoylation of 2,2,4-trimethyl-1,3-pentanediol in pyridine or any other suitable tertiary amine that functions as an HCl absorber, using an approximately equimolar amount of benzoyl chloride or alkyl-substituted benzoyl chloride. In this method, preferably carried out in a suitable solvent, such as carbon tetrachloride for example, the acid chloride is combined with a solution of TMPD and amine at a rate sufficient to control the exothermic heat of reaction, using external cooling means if and as necessary. Once the benzoylation step has been completed, the resulting reaction mixture is washed with an aqueous solution of an acid, such as phosphoric acid for example, to remove by-product amine hydrochloride and any excess amine. The organic layer can then be washed with water and/or an aqueous alkaline solution to remove chloride ion, and stripped to remove solvent, as is well-known in the art. The product thus obtained can be used as such, if desired, but preferably is further purified by means of distillation.

In the benzoylation process, it is preferred to use a monomethylbenzoyl chloride or benzoyl chloride, and particularly preferred to use benzoyl chloride. However, the acid chlorides of any of the alkyl-substituted benzoic acids described above for use in transesterification, as well as benzoic acids, substituted in the 6-position, such as 2,6-dimethylbenzoic acid, 2,4,6-trimethylbenzoic acid, 2,3,4,6-tetramethylbenzoic acid and 2,3,4,5,6-pentamethylbenzoic acid can also be used if desired, as well as mixtures of any of the foregoing.

In addition to carbon tetrachloride, other solvents suitable for use in this process are any inert organic solvents, such as benzene, toluene, naphtha, halogenated hydrocarbons, and so forth. Any suitable water-soluble acid can be used, as an aqueous solution, for washing the reaction mixture, but inorganic acids are preferred.

The benzoate mono- and di-esters of TMPD as herein disclosed are useful for a variety of purposes for which esters are commonly employed, including use as lubricants, functional fluids, antimicrobial agents, and so forth. They are of particular utility and value as plasticizers for polymeric resins and synthetic rubbers. Such plasticized compositions can be fabricated into useful articles by any of the known methods, including molding, extrusion, calendering, and spread coating.

The term polymeric resins as used herein includes homopolymers and copolymers of: vinyl esters of carboxylic acids such as vinyl acetate, propionate and butyrate, esters of unsaturated acids such as methyl acrylate and methyl methacrylate; polyvinyl alcohol; polyvinyl butyral; polyvinylidene chloride, and cellulose esters and ethers.

A particular class of polymeric resins with which the mono-and di-esters of this invention are especially useful as plasticizers are the vinyl resins, by which is meant homopolymers of vinyl chloride and copolymers of vinyl chloride and one or more other mono- or di-olefinically unsaturated monomer copolymerizable therewith. Such other monomers include ethylene, propylene, vinylidene chloride, vinyl acetate, and methyl acrylate, by way of examples.

The vinyl resins are preferred as components of the plasticized resinous compositions which represent one embodiment of this invention. The plasticizer, monobenzoate ester of TMPD or dibenzoate ester of TMPD (which terms include esters of alkylbenzoic acids) or mixtures thereof in any proportions, can be used in amounts ranging from about 1 to about 200 parts by weight per hundred parts by weight of resin, depending on the properties desired. Generally, the amount of plasticizer will be from about 10 to about 100 parts per hundred parts of resin.

As will be apparent to those skilled in the art, such resinous compositions may, if desired, also contain any of the common additives in the usual amounts. Such additives include heat stabilizers, light stabilizers, lubricants, flame retardants, microbicides, impact modifiers, flow modifiers, anti-static agents, fillers, and pigments. Other known plasticizers such as phthalate esters, adipate esters, phosphate esters, epoxidized oils, and so forth can also be present in the resinous compositions without departing from the scope of this invention. All of the foregoing additives are optional and do not, per se, constitute a part of the invention.

This invention is further illustrated by, but is not to be considered limited by, the following examples.

EXAMPLE 1

Preparation of 2,2,4-Trimethyl-1,3-pentanediol Dibenzoate via Base-catalysed Transesterification a. Preferred Procedure: Catalysis by Lithium Amide/Sodium Methoxide

A suitable reaction vessel was charged with
584 g (4.00 m) of 2,2,4-trimethyl-1,3-pentanediol (TMPD)
1200 g (8.82 m) of methyl benzoate and
1.38 g (0.06 m) of lithium amide (1.5 mole % based on TMPD).

Vacuum was applied down to ca. 15 mm Hg while the mixture was heated to effect solution of the reactants at 50°–55° C. and volatilization of the methanol-of-reaction at 60° C. After methanol evolution had diminished over the course of two hours, the pot temperature was raised to 100° C. and maintained at this temperature and 15 mm Hg absolute pressure for another hour.

At this point, precipitated material identified as lithium benzoate had formed in the reaction mixture. This was indicative of a side reaction between methyl benzoate and the propagating methoxide ions required for continuing the transesterification; see, for example, Bunnett et al., J. Am. Chem. Soc. 72,2378 (1950).

In order to economically regenerate propagating alkoxide species, there was added to the reaction mixture
6.1 g (0.03 m) of a 25% solution of sodium methoxide-in-methanol
(solubilization of lithium also effected via formation of the more insoluble sodium benzoate) and heating at 100° C. and 15 mm Hg absolute pressure was continued for an additional two hours to carry the transesterification to a greater degree of completion. The vacuum was then increased down to an absolute pressure of 0.1 mm Hg at 100° C. in order to recover
127 g of methyl benzoate
as an overhead distillate. Unreacted TMPD as well as the last traces of methyl benzoate were removed by vacuum steam distillation at 125°–130° C. and 25–50 mm Hg after which the resulting crude product was washed with
300 g of 1% sodium carbonate solution.

The resulting organic layer was dried by vacuum stripping at 90°–95° C. and 15 mm Hg and vacuum-filtered with the aid of
5.2 g of diatomaceous earth
to obtain
1322 g of product
assaying (wt. %) as follows by gas chromatography:

| | |
|---|---|
| TMPD dibenzoate | 97.1% |
| TMPD monobenzoates | 2.7% |
| Minor components | 0.2% |

Based on the TMPD charged, this analysis corresponded to a 90.7% yield of the dibenzoate ester and a 94.2% yield of TMPD di/mono benzoate mixture with a high diester content.

b. Use of Lithium Amide as the Sole Catalyst

The above was carried out without the use of sodium methoxide as a secondary catalyst. From this system,
182 g of methyl benzoate
was recovered and there was obtained 1292 g of product
assaying as follows:

| | |
|---|---|
| TMPD dibenzoate | 84.3% |
| TMPD monobenzoate | 14.9% |
| Other components | 0.8% |

In this case, the yield of the dibenzoate was 76.9% while the yield of the TMPD di/mono benzoate mixture of high diester content was 96.2%.

c. Using Other Catalyst Systems

The above procedures were carried out using the following catalyst systems at the corresponding molar levels. Results are listed in Table I:

three hours, 65.5 g of overhead distillate was collected at a pot temperature ranging from 192° to 213° C. and a head temperature of 65°–70° C. (with a final rise to 117° C.). This distillate was found by gas chromatography to consist of 96.4% methanol and 3.5% water.

Workup according to Example 1a led to isolation of 284 g of product
assaying as follows:

| | |
|---|---|
| TMPD dibenzoate | 70.4% |
| TMPD monobenzoates | 15.2% |
| Other components | 14.4% |

These results corresponded to a 56.5% yield of the dibenzoate ester and a 73.8% yield of TMPD di/mono

TABLE I
PREPARATION OF TMPD DIBENZOATE USING OTHER CATALYST SYSTEMS

| CATALYST | PRODUCT COMPOSITION (Wt %) | | | YIELD (Mole % Based on TMPD) | |
|---|---|---|---|---|---|
| | TMPD Dibenzoate | TMPD Monobenzoate | Minor Components | TMPD Dibenzoate | TMPD/Di/Mono Benzoates |
| *Sole Catalysts (following Example 1b)* | | | | | |
| (1) Lithium methoxide | 67.7 | 30.9 | 1.4 | 57.9 | 95.4 |
| (2) Lithium hydroxide | 65.5 | 31.7 | 2.8 | 56.5 | 95.2 |
| (3) Monolithium ethyleneglycolate | 82.9 | 15.1 | 2.0 | 76.9 | 96.7 |
| (4) Sodium methoxide | 61.3 | 37.8 | 0.9 | 45.1 | 84.5 |
| (5) Magnesium ethoxide | | no reaction | | | |
| (6) Aluminium isopropoxide | | no reaction | | | |
| (7) Tetramethylammonium hydroxide | 85.7 | 13.0 | 1.3 | 81.2 | 98.7 |
| *Catalyst Combinations (following Example 1a)* | | | | | |
| (8) Monolithium ethyleneglycolate/Sodium methoxide | 94.5 | 4.5 | 1.0 | 90.6 | 96.7 |
| (9) Lithium diisopropylamide/Sodium methoxide | 90.5 | 7.7 | 1.8 | 79.2 | 88.7 |

The results on the foregoing base-catalysed TMPD/methyl benzoate transesterification reactions show a pattern of generally high yields of, and excellent selectivity for, TMPD benzoates. The products show quite low levels of minor components and yields less-than-quantitative appear to be due to unreacted TMPD rather than by-product formation resulting from degradation of TMPD or the TMPD esters.

All the systems described provided TMPD benzoate products having the diester component as the major product. However, the use of the combination catalyst systems in which sodium methoxide is used to regenerate propagating alkoxide species was especially effective for producing TMPD benzoate compositions with diester levels above 90%. Surprisingly, sodium methoxide as the sole catalyst appears to promote a slower rate of reaction.

EXAMPLE 2

Comparative Example: Preparation via Transesterification Catalysed by Butylstannoic Acid This example describes an acid-catalysed transesterification system using a weak acid/amphoteric-type catalyst. Thus, a mixture of
146 g (1.00 m) of TMPD
300 g (2.21 m) of methyl benzoate and
0.98 g (0.0047 m) of butylstannoic acid
was heated with agitation in a reactor equipped with a Goodloe-packed, 12"×1" fractionating column surmounted with a condensing system. Over a period of benzoates.

By trapping of a gas chromatographic peak, the main constituent of the other components was identified as a 2,2,4-trimethylpentenyl benzoate, a side reaction product resulting, apparently, from the catalyst-sponsored internal dehydration of the TMPD.

EXAMPLE 3

Comparative Example: Preparation of 2,2,4-Trimethyl-1,3-pentanediol Dibenzoate via Esterification Catalysed by Butylstannoic Acid In a similar manner, a weak acid/amphoteric catalyst system was used to promote the direct esterification of TMPD with excess benzoic acid. Thus, a mixture of
146 g (1.00 m) of TMPD
268 g (2.20 m) of benzoic acid
1.25 g (0.0060 m) of butylstannoic acid and
40 g of toluene
was heated with agitation. Over a period of 5–6 hours at a pot temperature (reflux) ranging from 197° to 212° C. (toluene removed as necessary to achieve temperature), 34.3 g (1.91 m) of water-of-reaction
was removed with the aid of a Dean-Stark trap.

The final reaction mixture was found to contain 0.50 mole benzoic acid per mole of TMPD charged and thus, 1.70 moles benzoic acid had reacted per mole of TMPD. This difference between the number of moles of water evolved and of benzoic acid consumed, viz. 0.21 mole/mole TMPD, was indicative of a competing internal dehydration reaction under the prevailing acidic conditions.

The residual benzoic acid was removed by washing with dilute (4-5%) aqueous alkali, vacuum stripped of volatile material at 100° C. and 15 mm absolute pressure to obtain, after filtration aided by 0.5% diatomaceous earth,
275 g of product
assaying as follows

| TMPD dibenzoate | 87.7% |
|---|---|
| TMPD monobenzoate | 1.5% |
| By-product | 9.8% |
| Minor components | 1.0% |

The yields of dibenzoate ester and the combined TMPD di/mono benzoates were therefore 68.1% and 69.8% respectively. Similarly to the previous example, the by-product was identified as 2,2,4-trimethylpentenyl benzoate.

EXAMPLE 4

Comparative Example: Preparation of 2,2,4-Trimethyl-1,3-pentanediol Dibenzoate via Esterification Catalysed by p-Toluenesulfonic Acid In order to show the effect of a strong acid catalyst on the course of the direct esterification of TMPD with benzoic acid, a mixture of
146 g (1.00 m) of TMPD
268 g (2.20 m) of benzoic acid
2.62 g (0.014 m) of p-toluenesulfonic acid and
40 g of toluene
was refluxed with agitation to collect, over a pot temperature range of 121°-148° C. and a period of ca. 9 hours
30.4 g (1.69 m) of water.
At this point, the evolution-of-water-of-reaction had ceased (short of the theoretical 2.00 moles water/mole TMPD)—possibly due to inter and/or intramolecular ether formation.

The resulting pot mixture was found to still contain 1.13 moles benzoic per mole of TMPD charged. In this case, therefore, only 1.07 moles benzoic acid had reacted per mole of TMPD.

Similarly to Example 3, these results were indicative of competing side reactions and workup in a similar manner led to
196 g of product
assaying as follows:

| TMPD dibenzoate | 7.2% |
|---|---|
| TMPD monobenzoate | 0.9% |
| By-product | 63.0% |
| Other components | 28.9% |

The yield of combined TMPD benzoates was therefore only 4.7% and, consistent with the preceding two examples, the by-product was identified as 2,2,4-trimethylpentenyl benzoate which, in this case, was formed to the extent of 53.2%. The other components were not identified but would appear to be products of side reactions derived from the TMPD.

By contrast with the base-catalysed transesterification systems, the acid-catalysed reactions furnished lower yields of TMPD benzoate products with accompanying by-product(s) formation resulting from degradation of the TMPD moiety. The system of Example 4, employing p-toluenesulfonic catalysis, was an extreme example of such degradation which, however, was also evident with the milder butylstannoic acid catalyst under the described laboratory conditions. In a scaled-up, commercial operation involving extended time/temperature cycles, it would be expected that the detrimental effect of butylstannoic acid or similarly mild tin or titanium catalysts would be more pronounced.

EXAMPLE 5

Preparation of 2,2,4-Trimethyl-1,3-pentanediol Monobenzoate Compositions a. Via Benzoylation in Pyridine

A suitable reaction vessel was charged with
584 g (4.00 m) of 2,2,4-trimethyl-1,3-pentanediol
383 g (4.85 m) of pyridine and
500 g of carbon tetrachloride.
The resulting mixture was stirred to effect solubilization and cooled with an ice/water bath to 5° C.
There was then added
620 g (4.41 m) of benzoyl chloride
over about 2.5 hours during which time the reaction temperature was maintained below 10° C. using external cooling. The resulting mixture was then agitated with a solution of
100 g of 85% phosphoric acid
in
2000 g of water
in order to extract the pyridine hydrochloride by-product and excess pyridine into the aqueous phase. The resulting organic layer was washed three times with
2 kg portions of water
to ca. pH 5 at which point a test for chloride ion in an aqueous extract was negative. Washing was continued using, in sequence, 2 kg portions of
0.8% potassium hydroxide solution and
water (3-5 times to pH 6-7).

The washed organic phase was vacuum stripped to remove solvent and subsequently distilled through a 6" Vigreaux column at 0.05 mm Hg absolute pressure to obtain, at a head temperature cut of 130°-132° C.,
717 g of distillate
assaying (wt. %) by gas chromotography as follows:

| TMPD monobenzoates | 98.2% |
|---|---|
| TMPD dibenzoate | 1.0% |
| Minor components | 0.8% |

Proton magnetic resonance analysis of this product indicated a 1/1 ratio for the two possible monobenzoate components, viz. the 2,2,4-trimethyl-3-hydroxypent-1-yl and 2,2,4-trimethyl-1-hydroxypent-3-yl benzoates.

b. Via Base-Catalysed Transesterification

A mixture of
146 g (1.00 m) of 2,2,4-trimethyl-1,3-pentanediol
150 g (1.10 m) of methyl benzoate and
1.02 g (0.015 m) of monolithium ethyleneglycolate
was reacted similarly to the procedure described in Example 1b. In this case, the final transesterification reaction mixture was submitted directly to the vacuum steam stripping step to obtain
30.3 g of an upper organic layer
containing (by gas chromatography) the following percentages of unreacted raw materials:

| | |
|---|---|
| TMPD | 95.9% |
| Methyl benzoate | 4.1% |

If suitably dried, this mixture of recovered raw materials could be recycled in a subsequent run. There was finally obtained
217 g of product
assaying as follows:

| | |
|---|---|
| TMPD monobenzoate | 52.2% |
| TMPD dibenzoate | 46.1% |
| Minor components | 1.7% |

Based on the TMPD charged, the yield of the TMPD benzoate species was 73.7% with 45.3% selectivity for the TMPD monobenzoates. With recycle of the TMPD recovered in the steam distillate, the yield of all TMPD benzoates obtained, based on the TMPD consumed, would by 91.9%.

EXAMPLE 6

Evaluation of Selected Plasticizer Compositions for Stain Resistance and Plasticizer Properties a. For Stain-Resistance Efficacy

Four plastisols, each containing a different plasticizer, were prepared by mixing the following ingredients in a high-intensity Cowles mixer at room temperature until a uniform dispersion of resin particles was obtained.

| | |
|---|---|
| Poly (vinyl chloride) resin | 100 |
| Epoxidized soybean oil | 3 |
| Stabilizer (liquid Ca—Zn complex stabilizer) | 3 |
| Plasticizer | 50 |

After thorough mixing, the plastisols were cast in films on coated paper and fused for two minutes at 170° C. The following five staining agents were then smeared on the fused films and allowed to stand at room temperature for two hours:
Driveway sealer
Shoe polish, brown
Felt-tip marker, black
Coal tar
Fabric dye, black
At the end of this period, the staining agents were wiped off with a paper towel wet with isopropyl alcohol.
Visual ratings of residual stains are shown in Table II.

TABLE II

| | STAIN RATINGS(1) | | | |
|---|---|---|---|---|
| | Films Containing as Plasticizers | | | |
| | Ex 1a Product | Ex 5a Product | DOP(2) | BBP(3) |
| Driveway sealer | 3+ | 0 | 5 | 4 |
| Shoe polish | 4 | 0 | 5 | 4 |
| Felt-tip marker | 4 | 0.5 | 5 | 4 |
| Coal tar | 1 | 0 | 5 | 4 |

TABLE II-continued

| | STAIN RATINGS(1) | | | |
|---|---|---|---|---|
| | Films Containing as Plasticizers | | | |
| | Ex 1a Product | Ex 5a Product | DOP(2) | BBP(3) |
| Fabric dye | 2 | 0 | 5 | 4 |

(1)Stain scale: 0 = none; 1 = very slight; 2 = slight; 3 = light; 4 = moderate; 5 = heavy.
(2)Bis (2-ethylhexyl) phthalate
(3)n-Butyl benzyl phthalate b. For Viscosity of Plastisols

Each of the above plastisol formulations was stirred for fifteen minutes after a uniform dispersion had been obtained. Viscosity was then measured with a Brookfield Viscometer, Model LVF, at a spindle speed of 20 rpm. Measurements were made at zero time and after aging at 25° C. for 24 and 48 hours. Results are shown in Table III.

TABLE III

| VISCOSITY OF PLASTISOLS | | | |
|---|---|---|---|
| Plasticizer Component | Initial | 24 hours | 48 hours |
| Ex. 1a product | 46000 | 53500 | 54500 |
| Ex. 5a product | 7600 | 11000 | 12800 |
| DOP | 4500 | 6280 | 10760 |
| BBP | 10000 | 41000 | 75000 | c. For Oven Heat Stability

Fused film specimens were placed on a Teflon sheet in a Warner-Mathis forced-air oven at 350° F. Color development is summarized in Table IV.

TABLE IV

| OVEN HEAT STABILITY AT 350° F. | | | | |
|---|---|---|---|---|
| | Color Rating* | | | |
| | Films containing plasticizers from | | | |
| Oven Time, Minutes | Ex 1a Product | Ex 5a Product | DOP | BBP |
| Initial | 0 | 0 | 0 | 0 |
| 10 | 1 | 1 | 1 | 1 |
| 20 | 2 | 2 | 2 | 2 |
| 30 | 5+ | 6+ | 6+ | 5 |
| 40 | 7 | 8 | 7 | 7 |

*Color Ratings: On a scale of 0 to 10, ranging from no discoloration (0), through yellow and brown, to black (10).

d. For Performance Properties

Performance properties on fused film specimens are summarized in Table V.

TABLE V

| PLASTICIZER PERFORMANCE | | | | |
|---|---|---|---|---|
| | Films containing plasticizers from | | | |
| Property | Ex 1a Product | Ex 5a Product | DOP | BBP |
| Gloss 60° (1) | 89.1 | 90.7 | 88.7 | 90.3 |
| Shore A Hardness (2) | | | | |
| Initial | 71 | 85 | 79 | 80 |
| 10 Sec. | 66 | 75 | 71 | 67 |
| Tensile Strength, psi (3) | 3500 | 3420 | 2260 | 2865 |
| Elongation, % (3) | 315 | 305 | 360 | 325 |
| 100% Modulus, | 2145 | 2000 | 1215 | 1145 |

TABLE V-continued
PLASTICIZER PERFORMANCE

| | Films containing plasticizers from | | | |
|---|---|---|---|---|
| Property | Ex 1a Product | Ex 5a Product | DOP | BBP |
| psi (3) | | | | |

(1) Measured with a BYK Chemie Gloss Unit
(2) ASTM D2240
(3) ASTM D638

The results set forth in Table II show that the two products of this invention, viz. TMPD mono- and dibenzoate, exhibit generally better stain-resistance performance than either bis (2-ethylhexyl) phthalate (DOP), a commodity plasticizer product, or n-butyl benzyl phthalate, a specialty plasticizer, both used in the flooring industry.

Tables III, IV and V show that the TMPD benzoates impart properties to plastisols and cured films which are in the range of those associated with accepted commercial plasticizer products.

What is claimed is:

1. Monoester compounds of the formula:

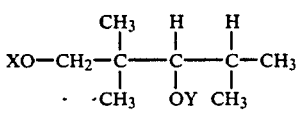

wherein X =

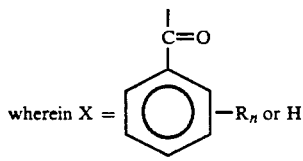

Y =

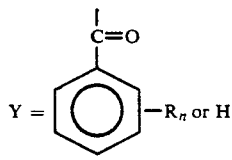

R is an alkyl group having from 1 to 4 carbon atoms, and n=0–5; with the proviso that when X is

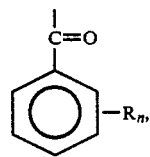

Y is H, and when Y is

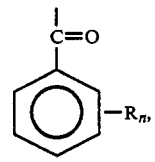

X is H.

2. Monoester compounds according to claim 1 wherein R is a methyl group and n is 1.

3. Compounds according to claim 1 comprising 2,2,4-trimethyl-3-hydroxypent-1-yl benzoate, 2,2,4-trimethyl-1-hydroxypent-3-yl benzoate, and mixtures thereof.

4. A plasticized resinous composition that comprises an admixture of at least one polymeric resin and a plasticizingly-effective amount of one or more of the compounds of claim 1.

5. A plasticized resinous composition according to claim 4 wherein the polymeric resin is selected from the group consisting of homopolymers of vinyl chloride, copolymers of vinyl chloride and at least one mono- or di-olefinically unsaturated monomer copolymerizable therewith, and mixtures thereof.

6. A plasticized resinous composition according to claim 5 wherein the plasticizing compound comprises one or more mono-esters of 2,2,4-trimethyl-1,3-pentanediol and a methylbenzoic acid.

7. A plasticized resinous composition according to claim 5 wherein the plasticizing compound comprises 2,2,4-trimethyl-3-hydroxypent-1-yl benzoate, 2,2,4-trimethyl-1-hydroxypent-3-yl benzoate, and mixtures thereof.

* * * * *